United States Patent [19]
Kell et al.

[11] Patent Number: 5,569,591
[45] Date of Patent: Oct. 29, 1996

[54] ANALYTICAL OR MONITORING APPARATUS AND METHOD

[75] Inventors: Douglas B. Kell, Aberystwyth; Andrew M. Woodward, Anglesey, both of United Kingdom

[73] Assignee: University College of Wales Aberystwyth, Aberystwyth, United Kingdom

[21] Appl. No.: 278,725

[22] Filed: Jul. 21, 1994

Related U.S. Application Data

[63] Continuation of Ser. No. 26,471, filed as PCT/GB91/01477 Aug. 30, 1991, which is a continuation-in-part of Ser. No. 975,928, Feb. 19, 1993, abandoned.

[30] Foreign Application Priority Data

Aug. 3, 1990 [GB] United Kingdom ............ 9018886
Jun. 3, 1991 [GB] United Kingdom ............ 9111893
Mar. 4, 1992 [GB] United Kingdom ............ 9204689

[51] Int. Cl.⁶ ............................................. C12Q 1/02
[52] U.S. Cl. ........................ 435/29; 435/14; 436/149; 436/151; 422/82.01; 204/403; 324/692; 205/792
[58] Field of Search ............... 435/14, 29; 436/63, 436/149–151; 422/82.01, 82.02; 204/153.1, 400, 403; 324/692, 71.1

[56] References Cited

U.S. PATENT DOCUMENTS

| | | | |
|---|---|---|---|
| 4,240,027 | 12/1980 | Larsen et al. | 324/57 R |
| 4,368,423 | 1/1983 | Liburdy | 436/63 X |
| 4,472,506 | 9/1984 | Liburdy | 436/63 |
| 4,801,543 | 1/1989 | Arnold et al. | 436/149 X |
| 4,919,770 | 4/1990 | Preidel et al. | 204/153.1 |

FOREIGN PATENT DOCUMENTS

| | | |
|---|---|---|
| B136965/78 | 12/1979 | Australia . |
| 0085327 | 8/1983 | European Pat. Off. . |
| 0101880 | 3/1984 | European Pat. Off. ....... G01N 33/48 |
| 131944A3 | 1/1985 | European Pat. Off. . |
| 3643263 | 7/1988 | Germany ............ G01N 33/493 |
| 8903616 | 7/1990 | Germany ............ G01N 27/02 |
| 89/08838 | 9/1989 | WIPO . |
| 9216835 | 1/1992 | WIPO . |

Primary Examiner—David A. Redding
Attorney, Agent, or Firm—Oppedahl & Larson

[57] ABSTRACT

Cellular biological material (such as living tissue) is analysed or monitored by applying an AC electrical potential across the biological material so as to produce a nonlinear dielectric spectrum, and obtaining a detectable signal corresponding to the resulting spectrum. The potential is of a first frequency and the measured response at one or more second frequency substantially not overlapping with the first frequency.

23 Claims, 13 Drawing Sheets

ANALYTICAL OR MONITORING APPARATUS AND METHOD

This application is a continuation of U.S. patent application Ser. No. 08/026,471 filed Mar. 4, 1993, which is a continuation-in-part of U.S. patent application Ser. No. 07/975,928 filed Feb. 19, 1993, now abandoned, which is the U.S. national phase of PCT patent application GB91/01477 filed Aug. 30, 1991.

BACKGROUND OF THE INVENTION

This invention relates to a method of analysis of biological cell materials and particularly, but not exclusively, to analysis or monitoring of materials comprising enzymes in membranes, as well as analysis of substrates for such cell materials and enzymes.

The linear passive audio and radio frequency electrical properties of biological cell materials are well known. In the frequency range below about 10 MHz, these properties are conveniently measured as the equivalent parallel conductance and capacitance of an electrochemical cell containing the system under study. Up to these radio-frequencies, most biological cell materials exhibit two major dispersions, known as the alpha and beta dispersions. Whilst other sub-dispersions contribute to these major dispersions, and may occasionally be separated from them, the beta dispersion of tissues and cell suspensions is caused predominantly by the build-up of charge at the essentially non-conducting plasma membrane surfaces. The alpha dispersion, though not always dependent upon the ionic strength of the medium, is usually accounted for mainly in terms of the relaxation of counter-ions tangential to the charged surfaces of the membrane and cell envelope.

In the simplest case of dielectric relaxation, that of the reorientation of a "hard" sphere with a permanent dipole moment, the statistical mean of the cosine of the angle which the dipole makes with the field, has a field-dependence following the Langevin function:

$$\cos \langle \theta \rangle = \coth x \times 1/x,$$

where $x=\mu E/kT$. A Taylor expansion of this series shows that substantial deviations from linearity do not occur for values of x less than approximately 1, and that to an excellent approximation $\cos \langle \theta \rangle = \mu E/3 kT$. Thus the dielectric displacement current is proportional to the magnitude of the exciting field, and their ratio, the admittance, independent of it. These properties are characteristic of a linear system obeying the fluctuation-dissipation theorem.

Due to the fact that they are suspended or dissolved in conductive aqueous media, biological dielectrics are "lossy". Thus electrochemical reactions, and especially Joule heating, restrict the AC voltages that may be applied to them, and the dielectric properties of biological cell materials are typically measured using macroscopic electrical fields E of the order 0.1–5 V.cm$^{-1}$. Given the effective dipole moments usually encountered, the Langevin factor $\mu E/kT$ is normally minuscule, and, as judged by the independence of the measured admittance from the exciting field, well within the range of linearity.

It is known to measure the linear properties of biological materials using impedimetric instruments designed to filter out currents and voltages at frequencies other than the fundamental. This results in materials which appear to have linear characteristics but are in fact non-linear dielectrics.

SUMMARY OF THE INVENTION

We have surprisingly found that, by applying a pure sinusoidal AC current to excite a biological cell material, if instead of observing the AC current only at the frequency applied, the entire frequency range of interest is observed, a non-linear dielectric spectrum may be produced from a biological material at voltage levels at which hitherto, the material has been expected to exhibit linear properties only.

The entire frequency range of interest may be studied by performing a transformation on the signal, for example a Fourier transform.

According to a first aspect of the invention there is provided a method of analysing biological cell material, substrates therefor or inhibitors of cell metabolism for such cell material, which method comprises causing an AC electrical potential across a sample of the biological material so as to produce a non-linear dielectric spectrum, and obtaining a detectable signal corresponding to the spectrum obtained.

According to a second aspect of the invention, there is provided a method of analysing biological cell material, substrates therefor, or inhibitors of cell metabolism for such cell material, which comprises causing an electrical potential of one or more initial frequencies to fall across the biological material, and measuring the response of the material at at least one response frequency, wherein the at least one response frequency is substantially not overlapping with the initial frequency or frequencies.

According to a third aspect of the invention, there is provided a method of analysing or monitoring a determinand associated with cellular biological material, which comprises applying an AC electrical potential at one or more discrete initial frequencies to a sample of said material; measuring a response of the material at at least one response frequency substantially not overlapping with said applied AC potential; and comparing said response with a stored characteristic of said determinand.

The determinand may be a concentration or other variable (or indeed parameter) in cellular biological material (such as viable or living tissue in, for example, an animal, such as a human animal). A preferred determinand is glucose concentration in, for example, blood.

The means for comparing the response to a stored characteristic of the determinand is typically data processing apparatus, such as a computer or the like, which has been previously calibrated with a characteristic of a determinand of cellular biological material of the same general type (such as a human patient) as will be described in more detail hereinafter. It is therefore not necessary in this embodiment of the invention to provide a reference non-linear dielectric spectrum; the apparatus may be calibrated by techniques described hereinafter for a first subject, and then used for further subjects of the same type.

The method according to the invention can be used, by way of example, for monitoring the ability of living or viable cell material to transduce exogenous electric field energy. We have discovered that the particular harmonics present in the non-linear dielectric spectrum obtained from a cellular biological material are indicative of the metabolic state of living cells in the biological material.

The AC potential may be applied by a plurality of appropriate electrodes, a coil or the like, generally of known type; the electrodes may be arranged to be substantially flush with the skin of a patient so that the apparatus can be used for non-invasive monitoring of physiological parameters of the patient.

A reference non-linear dielectric spectrum may be produced in some embodiments using the supernatant of a biological material, the conductivity of which is adjusted to be substantially identical to that of the sample of the biological material. The spectrum from the sample is then divided by the reference spectrum, resulting in the deconvolution of the effects due to non linearitics within the electrochemical system from those due to the biological cells themselves.

When a field of appropriately low frequency is applied to cellular material between two or more macroscopic electrodes, the charging of the membrane capacitance may cause a lesser but effective "amplification" of the macroscopic field across the membrane. In certain cases in which the membrane of interest contains appropriate enzymes this can cause performance of useful biological work in a field and frequency-dependent fashion. A general mechanism underlying this effect is that enzymes are not dipolar "billiard balls" and can relax between different conformations, some of which may and some of which may not have different vectorial dipole moments from each other.

The electrical potential applied to the biological material may comprise a relatively high field applied to excite the material and a relatively low probing AC voltage to register the field-dependent dielectric properties of the material.

Preferably, however, a sinusoidal AC current is used to excite the material and the entire frequency range of interest is observed by performing a transformation to see the extent to which the non-linearities of the sample are manifest by the generation of harmonics. By varying the frequency and amplitude of the exciting current, a multi-dimensional non-linear dielectric spectrum can be built up which can act as a dielectric fingerprint of the sample under test.

The third harmonic of the non-linear dielectric spectrum may sometimes be of particular interest; its magnitude may be indicative of the concentration of cells in the biological sample. The invention thus provides a method of observing the third harmonic in a non-linear dielectric spectrum obtained from a biological sample. It also provides a method of determining the concentration of cells in a cell suspension, since the magnitude of the third harmonic is indicative of the concentration of cells in such a suspension. The invention also provides a method of monitoring the ability of living cells to transduce exogenous electric field energy. We have discovered that the particular harmonics present in the non-linear dielectric spectrum obtained from a biological sample are indicative of the metabolic state of living cells in a biological sample.

Membrane proteins (typically in living tissue) are particularly powerful candidates for interacting with electrical fields, for several reasons, including the following:

(i) the membrane protein cannot rotate from one side of the membrane to the other and dissipate electrical energy by simple Debye-like rotation of this type;

(ii) as described above, the membrane can "amplify" the exciting signal; and (iii) membrane proteins have substantial dipole moments.

In addition, of course, in common with all proteins, they can effect transitions between different conformational states possessing different dipole moments. Thus in seeking a mechanistic basis for the remarkable generation of non-linear dielectric spectra that we have observed one is led to consider the membrane properties of cell material present in the biological material under test.

There is further provided by the present invention apparatus for carrying out a method as hereinbefore described, which apparatus in a first embodiment, comprises:

(a) retaining means for retaining a sample of living cell material;

(b) means for applying an AC electrical potential across said sample so as to produce a non-linear dielectric spectrum; and (c) means for obtaining a detectable signal corresponding to said spectrum.

In a second embodiment there is provided apparatus for monitoring or analyzing a determinand associated with cellular biological material, which apparatus comprises:

(a) means for applying an AC electrical potential at one or more discrete frequencies to said material;

(b) means for determining a response of said material at one or more frequencies which were substantially absent from the applied AC potential; and (c) means for comparing said response to a stored characteristic of said determinand.

The apparatus according to the invention is, in one embodiment, preferably provided with means for obtaining a detectable signal, which may, for example, include a chart recorded, screen display or the like.

Apparatus according to the second embodiment of the invention preferably comprises means for retaining the biological material in proximity to the electrical potential applying means; such means may, for example, be adhesive provided on a patch or the like for retention of an electrode to a patient's skin.

The production of power spectra using Fourier transformation results in the loss of phase information, and therefore only the magnitude of the 3rd harmonic (or indeed of any other harmonics) is used to display the energy transduced by the cells from the fundamental to the given harmonic in the present system. The cells do not "harvest" energy from the 3rd harmonic present in the exciting signal since no harmonics are observed when the fundamental voltage or frequency of the exciting signal are changed to those generated by our signal source when the fundamental is set as 2 $V.cm^{-1}$ and 20 Hz. Thus, variations in the magnitude of a harmonic may be caused by variations in its absolute magnitude and/or its phase relative to that of the 3rd harmonic present in the exciting signal. The data are present in logarithmic (dB) scale, since this serves to accentuate the precision with which alterations in the observable magnitude of harmonics may be recorded.

Whilst in some embodiments (such as in the monitoring of yeast culture) there may be some day-to-day variation in the exact magnitude of the 3rd harmonic (when viewed on the logarithmic decibel scale), the data obtained are very reproducible within a few dB, particularly for a given batch of cells. Similarly, using identical "samples" (or "reference" supernatants) in both electrochemical cells, no harmonics are observed, (i) indicating that the surface electrochemistry of their electrodes is well-matched, and (ii) that living cells are indeed the source of the 3rd harmonic observed.

The electrical fields involved in the following experiments are (in terms of the Langevin factor) quite minuscule, and the system would normally be expected to lie well within the domain of linearity. Indeed, observations of the fundamental, and linear impedance measurements using a Hewlett-Packard 4192A Impedance Analyser indicated that the linear impedance was independent (within experimental error) of the magnitude of the exciting voltage in the range studies. Thus, it is quite feasible to have a system in which the impedance appears linear but which is in fact non-linear. The potential-dependent capacitance (thickness) of a bilayer membrane can exhibit a quadratic dependence upon the potential difference across it. However, at the potentials used here the quadratic term is negligible.

Membrane proteins are particularly powerful candidates for interacting with electrical fields for a variety of reasons, including the following: (i) the membrane protein cannot rotate from one side of the membrane to the other and dissipate electrical energy by simple Debye-like rotation of this type; (ii) as described above, the membrane can "amplify" the exciting signal; (iii) membrane proteins have substantial dipole moments. In addition, of course, in common with all proteins, they can effect transitions between different conformational states possessing different dipole moments. Thus in seeking a mechanistic basis for the remarkable generation of nonlinear dielectricity that we have observed one is led to consider the membrane properties of this organism.

A washed cell suspension of S. cerevisiae with no added carbon substrate, slowly metabolising endogenous stores under the presumably essentially anaerobic conditions pertaining in the relatively concentrated suspensions normally used, may be expected to generate ATP by substrate-level phosphorylation. As a major potential mechanism of "slip" or "overflow metabolism", this ATP may be expected to be utilised by the $H^+$-ATPase present in this organism to drive the uptake of cations such as $K^+$ from the external medium until a state of "static head" is attained, in which the free energy of hydrolysis of ATP is balanced against the free energy stored in the $K^+$ gradient (and indeed those of other ions). The distribution of enzymic conformational macrostates would then be approximately determined by their basic free energies and the net turnover (rate of entropy production) of the enzyme would be minimal. In this sense the energetic macrostates of the enzyme may then be regarded as a symmetrical potential well. This would then explain the generation of odd but not even harmonics. We have determined that the $H^+$-ATPase in the plasma membrane of this organism, as the main enzyme potentially active under the physiological conditions used, is the major source of the nonlinear dielectric response observed.

We have shown for the first time in cell suspensions that the conformational flexibility of enzymes can manifest in the generation of nonlinear dielectric spectra at very modest values of the exciting field, in which the Langevin factor is extremely small and in which purely linear behaviour would formerly be expected.

BRIEF DESCRIPTION OF THE DRAWINGS

The invention will now be described, by way of example only, with reference to the accompanying drawings, in which.

DETAILED DESCRIPTION OF THE INVENTION

Figure 1:
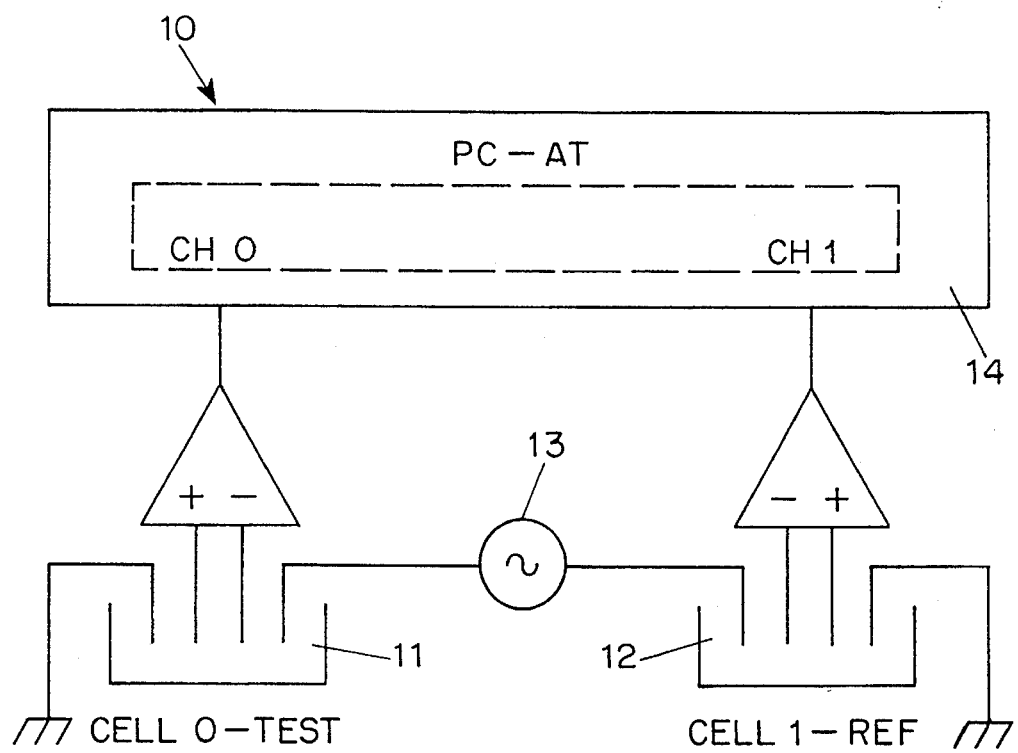
FIG. 1 is a schematic representation of a non-linear dielectric spectrometer for carrying out the method according to the invention.

Referring to FIG. 1, a non-linear dielectric Spectrometer for use in carrying out the method according to the invention is designated generally by the reference numeral 10. The spectrometer 10 comprises two electrochemical cells 11, 12. Cell 11 is a test cell containing a sample of the biological system whose nonlinear dielectric properties are being studied. In this example the biological system comprises a system comprising a suspension of S. cerevisiae. The cell concentration was approximately 50 mg dry wt. $ml^{-1}$ in a medium of 20 mM $KH_2PO_4$, 30 mM KCl, 1 mM $MgCl_2$ pH 6.5. Tests were carried out within four hours of preparing the suspension. Cell 12 is a reference cell comprising the supernatant of the test suspension, the conductivity of which was adjusted with distilled water to compensate for the volume fraction of cells present in the sample, to be identical to that of the sample at the frequency of interest. The cells 11, 12 were connected to a sinusoidal oscillator 13, via a Data Translation Analog to Digital converter, to an 80386 microcomputer 14.

The system was built around an IBM-PC-AT compatible microcomputer (Viglen III, 80386 main processor from Viglen Ltd, London U.K.). To maximise the performance of the mathematical operations, an 80387 co-processor (Cyrix 83C87) was used. One of the expansion ports of the computer was furnished with a Trada Data Translation model 2823 ADC/DAC board. Because of the expectation that the harmonic signals would have a low magnitude, a 16-bit board was chosen with 4 differential inputs and a stated upper frequency of 100 kilosamples/second.

Figure 2:
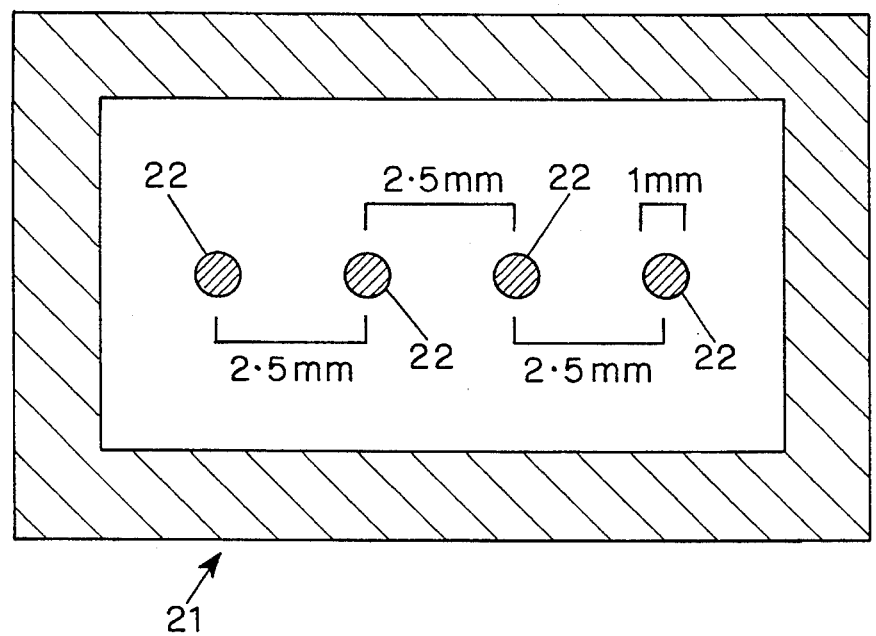
FIG. 2 is a schematic representation of the electrochemical cell used in the spectrometer of FIG. 1.

Referring to FIG. 2, an electrochemical cell 21 is shown. To minimise the contribution of electrode polarisation phenomena a 4-electrode system based on gold pin-type electrodes 22 was used. Signals were applied to the outer, current electrodes by means of a Thandor TG501 function generator (RS Components Limited). The frequency and amplitude of these signals were checked using a Solartron 1200 Signal Processor (Schlumberger Instruments, Farnborough, Hants) and a Hameg HM 208 Digital Storage Oscilloscope.

The acquisition of the data and its subsequent processing and display was, in some embodiments, performed using ILS software (Signal Technology Inc, Goleta, Calif.) running under control files.

The spectra were collected using the following method:

The sample cell suspension was pipetted into the electrode cell 11 (FIG. 1), the test waveform applied to the (outer) current electrodes, and the data logged from the (inner) voltage electrodes at a sampling frequency (which was typically at 25 times the frequency of the fundamental) and for a time specified by the operator. Time was specified in terms of a number of blocks, each block consisting of 512 samples. At the end of the time specified, the data were Fourier transformed as follows. Preliminary pre-whitening was carried out by subtracting the mean of the block from the individual samples. Each block was then windowed using a Blackman window and fast-Fourier-transformed using routines within the ILS software to form an ensemble of power spectra. These were then averaged in order to enhance the signal:noise ratio. The spectral data were stored on the computer's hard disk.

Figure 3:
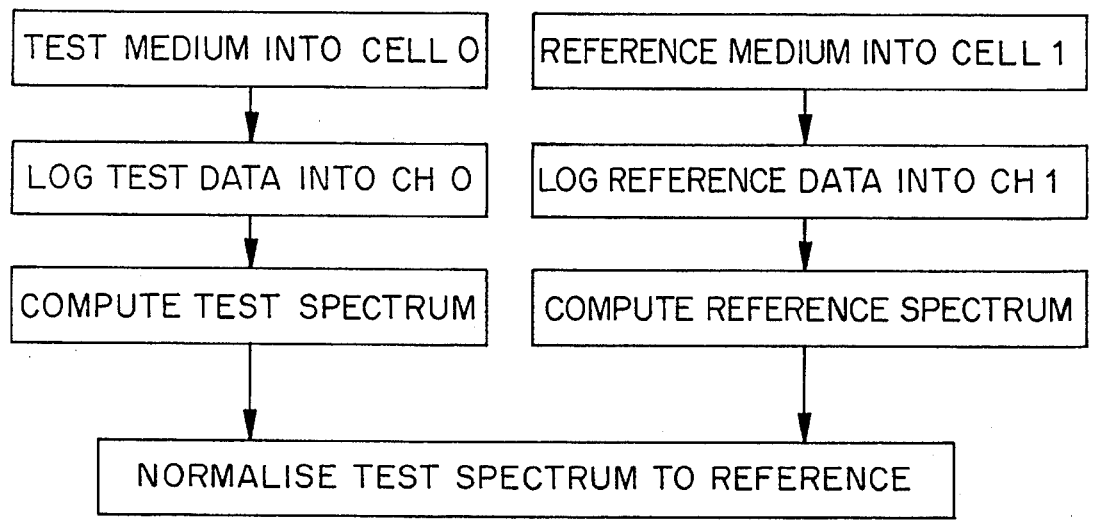
FIG. 3 is a block diagram of a particular method used to obtain non-linear dielectric spectra uncontaminated by artefactual electrochemical phenomena.

A reference spectrum was acquired using the supernatant in cell 12 (FIG. 1), whose conductivity had been adjusted (with distilled water), to compensate for the volume fraction of cells present in the sample to be identical to that of the sample at the frequency of interest. Two different types of control file were used, depending upon whether the reference was to be logged using the same set of electrodes or (as was done in some of the experiments described herein) a separate matched cell. In either case, the logging, windowing and Fourier transformation routines were identical, and provided a power spectrum of the "reference" cell, which was also logged on the computer's hard disk. Finally the "sample" power spectrum so obtained was divided by the "reference" power spectrum, and also stored on the disk. The total time necessary to acquire a difference dielectric spectrum (at 20 Hz, 500 samples per second for 10 blocks) was some 2.5 minutes. A diagram of the steps involved in the generation of the non-linear dielectric spectra is shown in FIG. 3. The advantage of this approach was that it allowed the effects due to nonlinearities within the electrochemical system from these due to the biological cells themselves to be deconvolved.

The spectrometer 10 may be used for the registration of non-linear biological dielectric spectra, to indicate for the first time that they are easily observed in cell suspensions, and to show that the $H^+$-ATPase in the plasma membrane of Saccharomyces cerevisiae is the source of the majority of the non-linear dielectric response thus observed.

Figure 4:
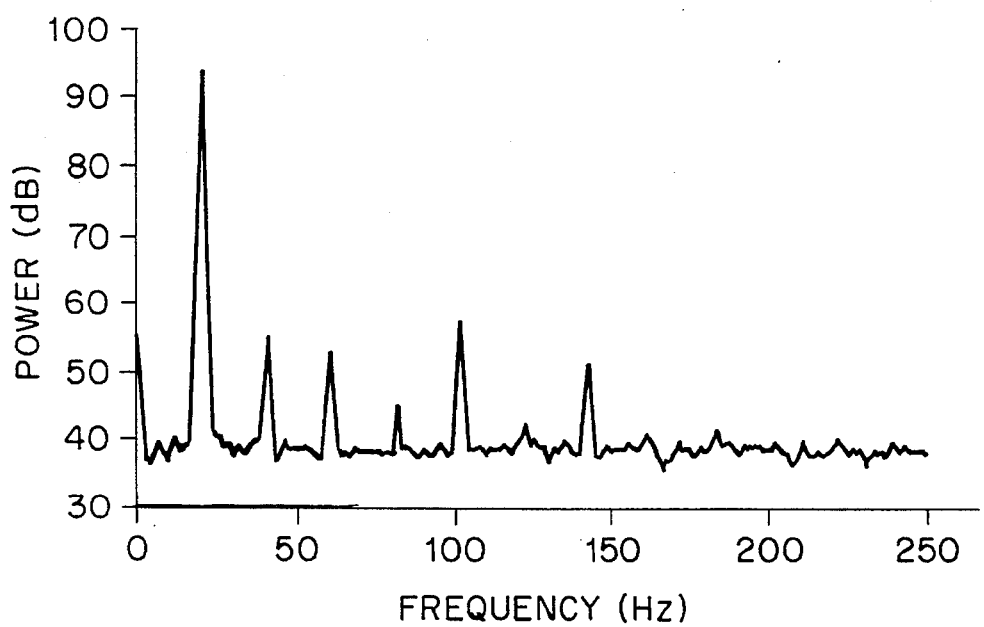
FIG. 4 is a representation of a non-linear dielectric spectrum of Saccharomyces cerevisiae (S. cerevisiae)
Figure 5:
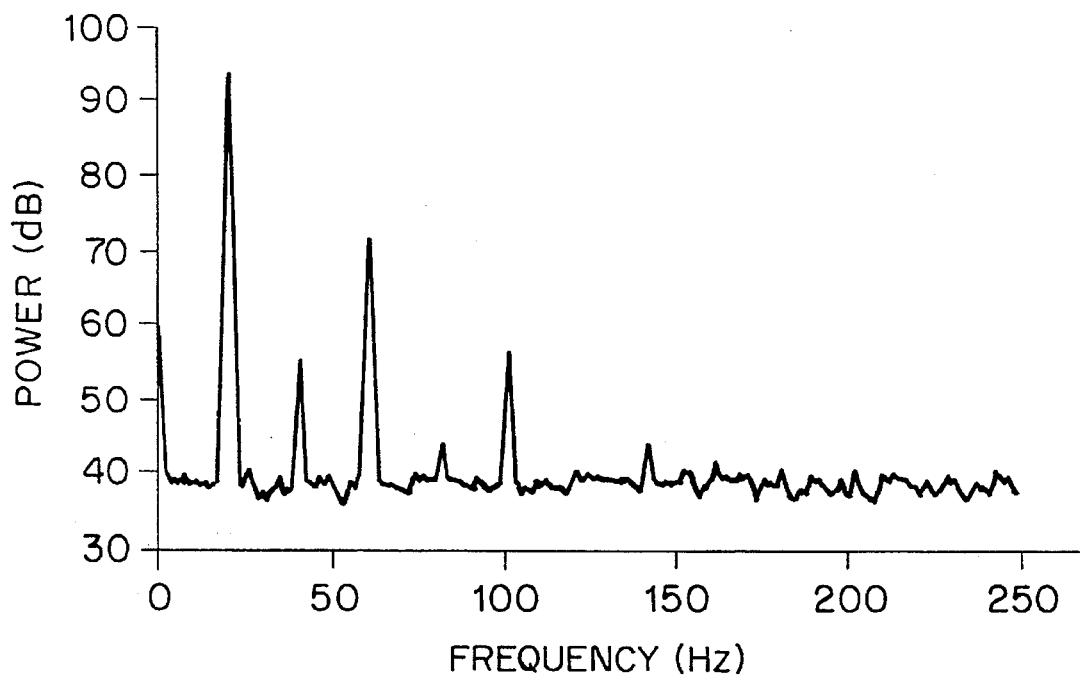
FIG. 5 shows a non-linear dielectric spectrum obtained from a reference cell.
Figure 6:
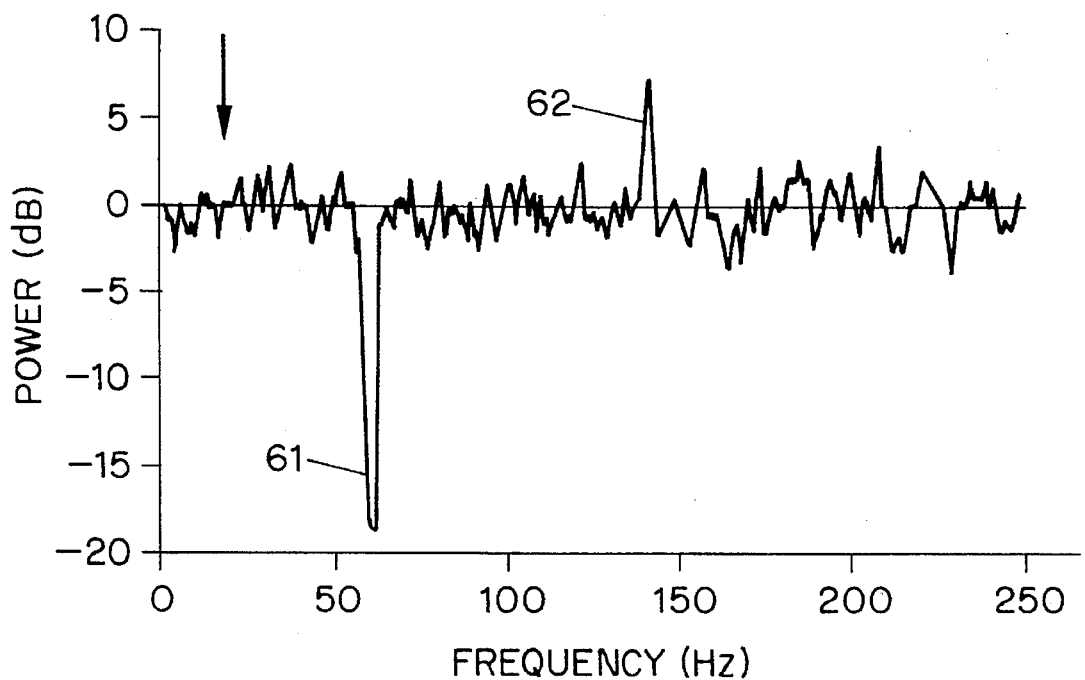
FIG. 6 shows a spectrum obtained by subtracting the spectrum of FIG. 4 from the spectrum of FIG. 3.

FIG. 4 shows a typical non-linear dielectric spectrum obtained from a suspension of resting cells of S. cerevisiae using the spectrometer of FIG. 1, with an exciting voltage (measured between the outer electrodes) of 1.5 V (2.0 V.cm$^{-1}$) at a frequency of 20 Hz, and displays spectra from the sample (FIG. 4) the reference (FIG. 5) and their difference (FIG. 6). Due to imperfections in the generator and the nonlinearities inherent in electrochemical systems, the applied waveform is not purely sinusoidal but contains harmonic components which, although very small by comparison with the energy in the fundamental, may yet be observed using a measuring system with the present (16-bit) sensitivity and a logarithmic display. The pattern of harmonics between the "sample" and "reference" cells is markedly different, and upon subtraction of the reference spectrum from the sample spectrum a very strong anti apparently negative third harmonic 61 (FIG. 6) is obtained. A (positive) 7th harmonic 62 is also reproducibly observed (and on occasion an 11th harmonic), but even harmonics are substantially absent under the stated conditions.

Figure 7:
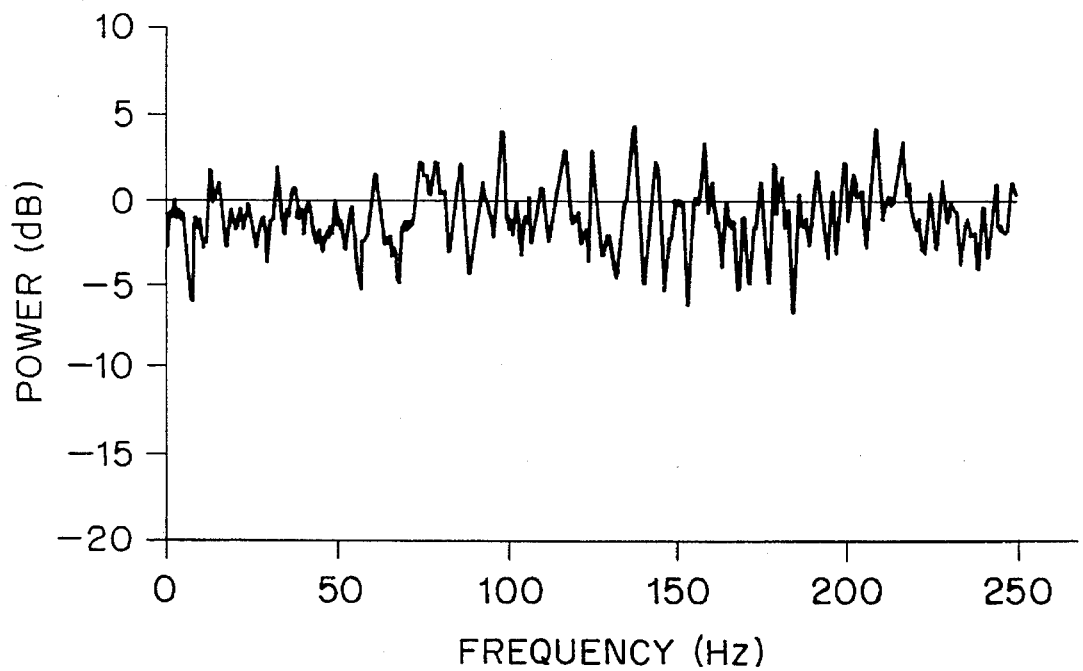
FIG. 7 is a non-linear dielectric spectrum obtained from a suspension of boiled cells.

Because of the use of the reference spectrum method, it was clear that the generation of a 3rd harmonic depended upon the presence of yeast cells. FIG. 7 shows that no third harmonic is generated using dead (boiled) cells. This indicated that the presence of potentially active enzymes was a prerequisite to the generation of a third harmonic.

Figure 8A:
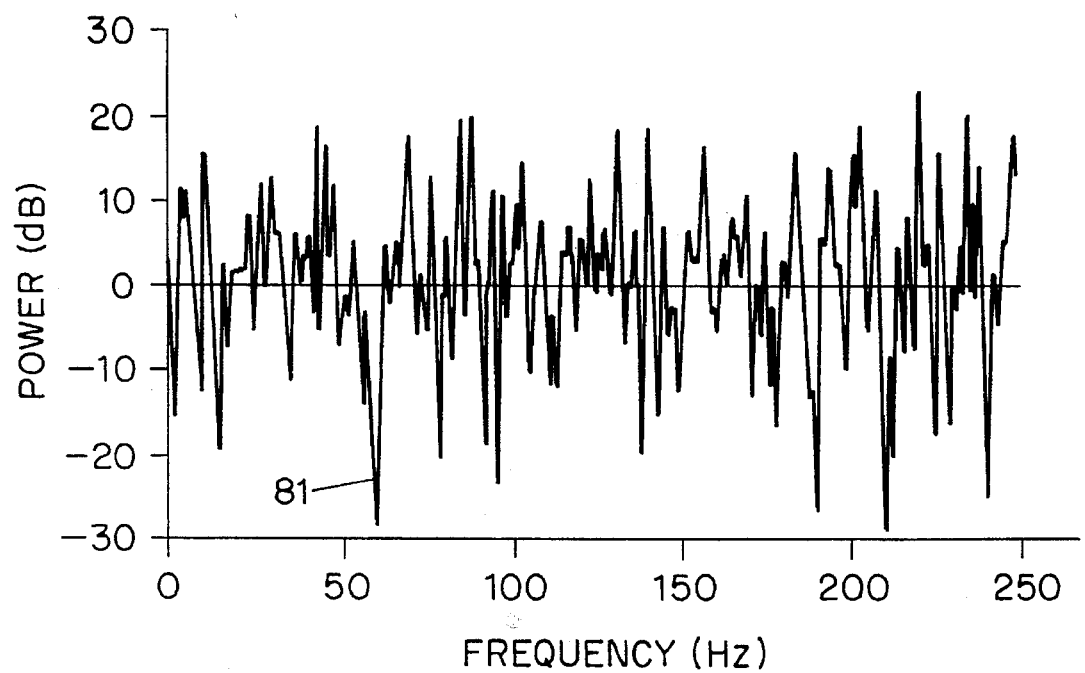
FIGS. 8(a)–(c) show the effect of averaging on the non linear dielectric spectrum of S. cerevisiae.
Figure 8B:
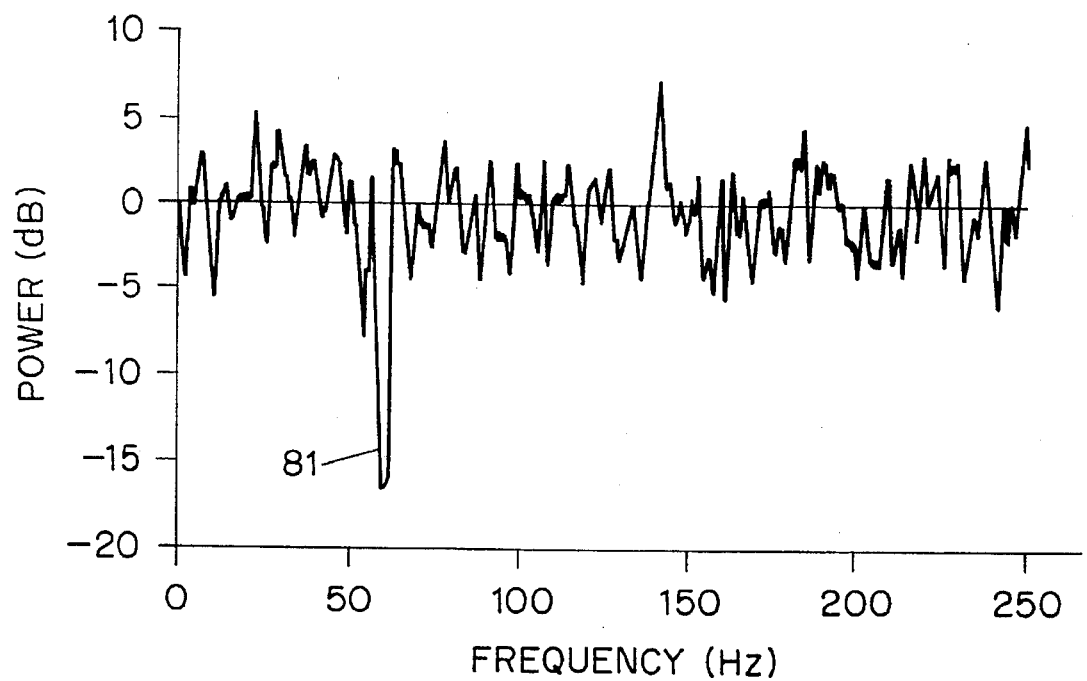
Figure 8C:
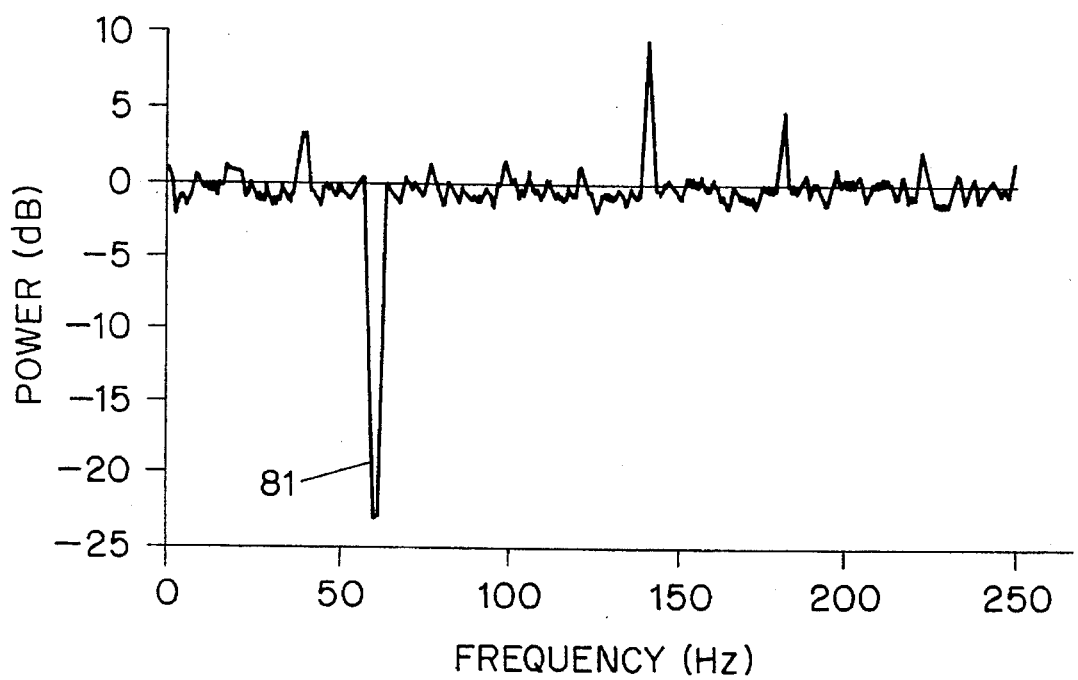

To establish whether only harmonics were generated, or whether the power spectra contained non-harmonic components, the number of blocks that were averaged was varied. The data from a representative set of runs are displayed in FIGS. 8a to 8c where it may be observed that the magnitude of the 3rd harmonic 81 remains essentially constant in the face of a highly variable degree of noise, the variance of the noise decreasing (as expected) in proportion to the number of blocks, such that no true non-harmonic components could be discerned.

Figure 9:
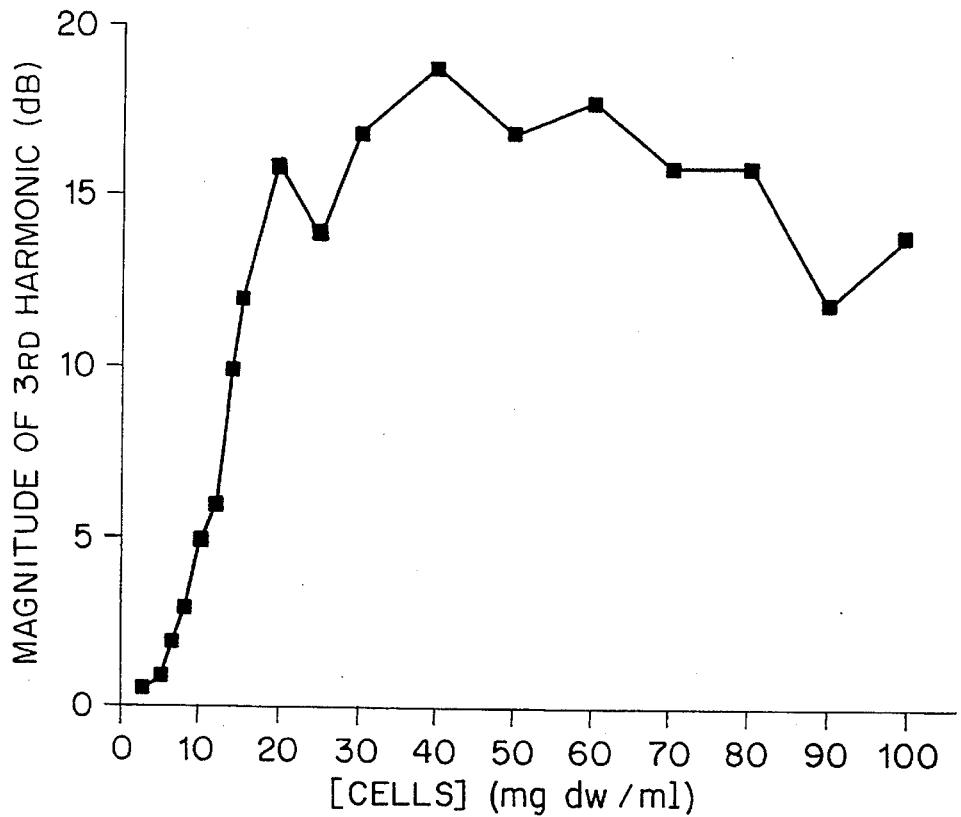
FIG. 9 shows the effect of cell concentration on the magnitude of the third harmonic in the non-linear dielectric spectrum of S. cerevisiae.

The dependence of the magnitude of the 3rd harmonic as a function of the concentration of cells is shown in FIG. 9 where it may be observed that the magnitude of the 3rd harmonic in dB is substantially linear with the concentration of cells up to a cell concentration of some 25 mg dry wt. ml$^{-1}$ whereupon a transition to a plateau region may be observed.

Figure 10:
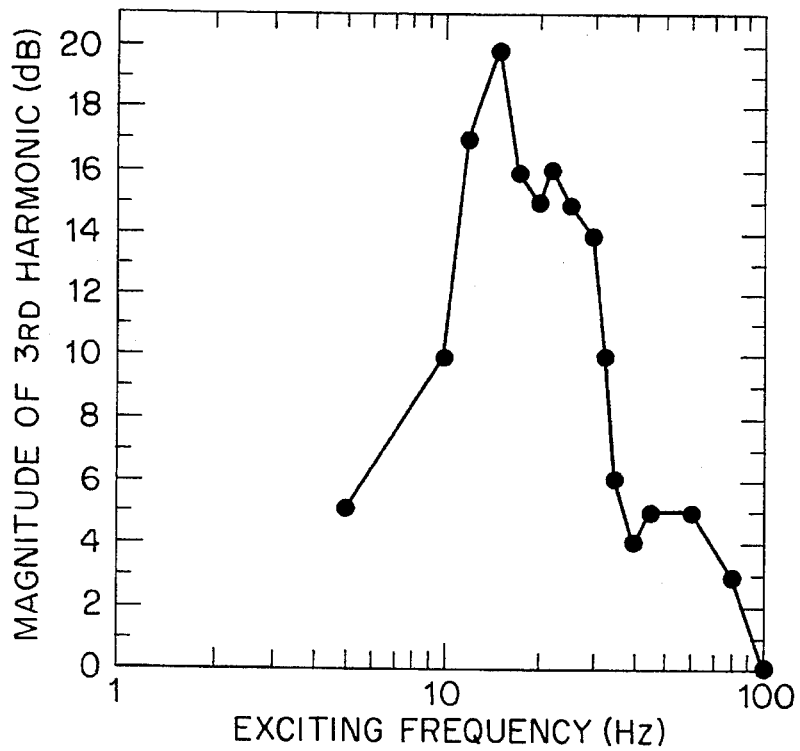
FIG. 10 shows the effect of exciting frequency on the magnitude of the third harmonic of the nonlinear dielectric spectrum of S. cerevisiae.

The 3rd harmonic generated was usually maximal when the exciting frequency was some 15–20 Hz. FIG. 10 displays the magnitude of the 3rd harmonic as a function of the exciting frequency. It may be observed that as the frequency is increased above or decreased below some 15–20 Hz, the magnitude of the 3rd harmonic drops off rather sharply.

Figure 11:
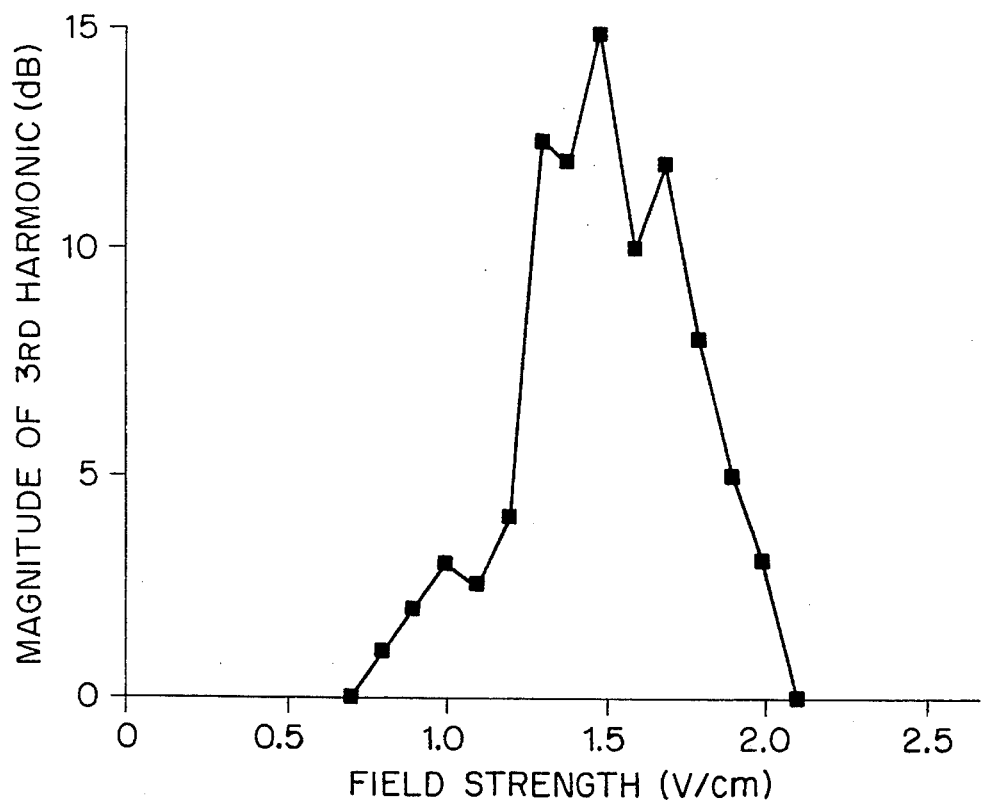
FIG. 11 shows the effect of the strength of the exciting field on the magnitude of the 3rd harmonic of the non-linear dielectric of S. cerevisiae.

As well as the above frequency window, there was an even sharper voltage or amplitude window within which nonlinear dielectric behaviour could be observed. FIG. 11 shows that the magnitude of the 3rd harmonic is only significant in a voltage window between about 0.6 and 2.1 V (0.8–2.8 V.cm$^{-1}$). When the exciting frequency was varied, the amplitude window observed did not appear to change significantly (data not shown). If the measurement was carried out in the presence of an additional electrostatic (DC) field, the magnitude of the 3rd harmonic was strongly decreased, disappearing completely when the DC field exceeded 0.4 V.cm$^{-1}$ (and the exciting AC field was 2.0 V.cm$^{-1}$).

It is well known that the catalytic cycle of enzymes of this type (the so-called $E_1E_2$ enzymes) involves an enzyme-bound phosphate intermediate, and that their activity can be inhibited by low concentrations of pentavalent vanadium compounds whose trigonal bipyramidal structure is thought to mimic the transition state of the phosphate during its hydrolysis, trapping the enzyme in its $E_2$ conformation.

Figure 12:
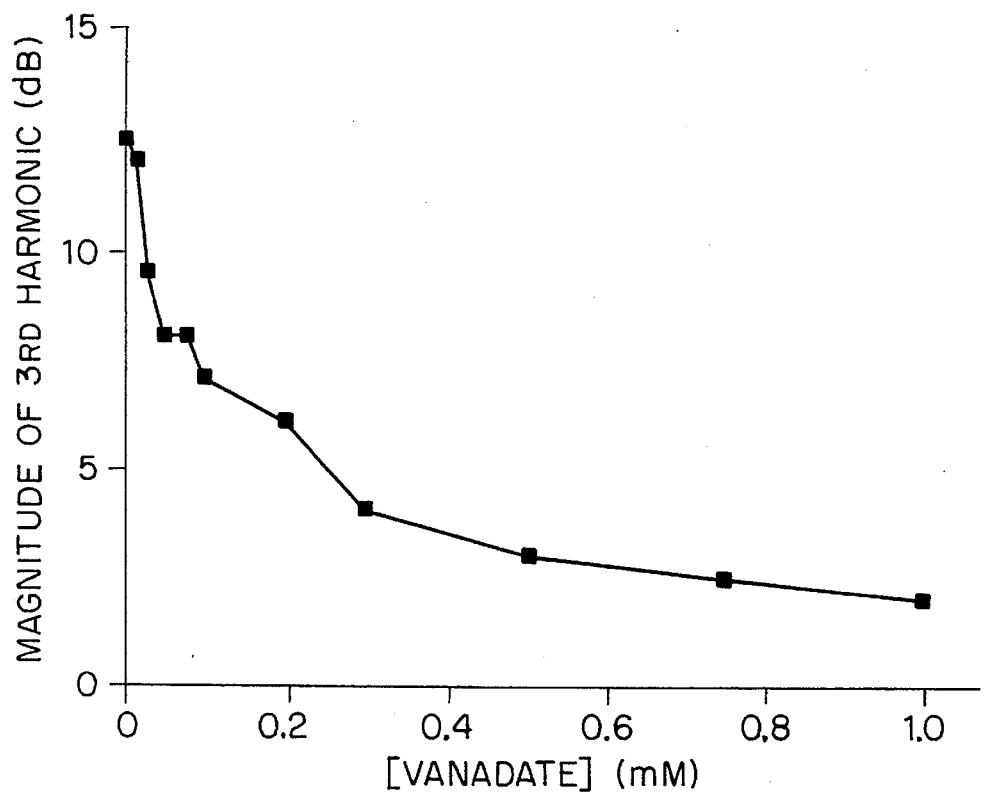
FIG. 12 shows the effect of sodium metavanadate on the magnitude of the third harmonic of the non-linear dielectric spectrum of S. cerevisiae.

FIG. 12 shows the effect of quite modest concentrations of vanadate on the magnitude of the 3rd harmonic, where it may be observed that the generation of this harmonic is essentially completely abolished by 1 mM sodium metavanadate, and with a $K_i^{app}$ (when the ordinate is plotted using a dB scale) of approximately 0.15 mM. This again suggests strongly that the $H^+$-ATPase in the plasma membrane of these cells is the main source of the non-linear dielectric response, and further serves to leave phenomena such as dielectrophoresis as the source of the non-linearities observed. The harmonics were also completely abolished by the H+-ATPase inhibitor dibenzhydryl carbodiimide at a concentration of 0.2 pmol/mg dry wt of cells. In a mutant strain of yeast having a vanadate-resistant ATPase, we have found that the generation of harmonics is also vanadate resistant, which is powerful evidence that the H+-ATPase may be the major source of the non-linear dielectric effect in this organism.

Figure 13:
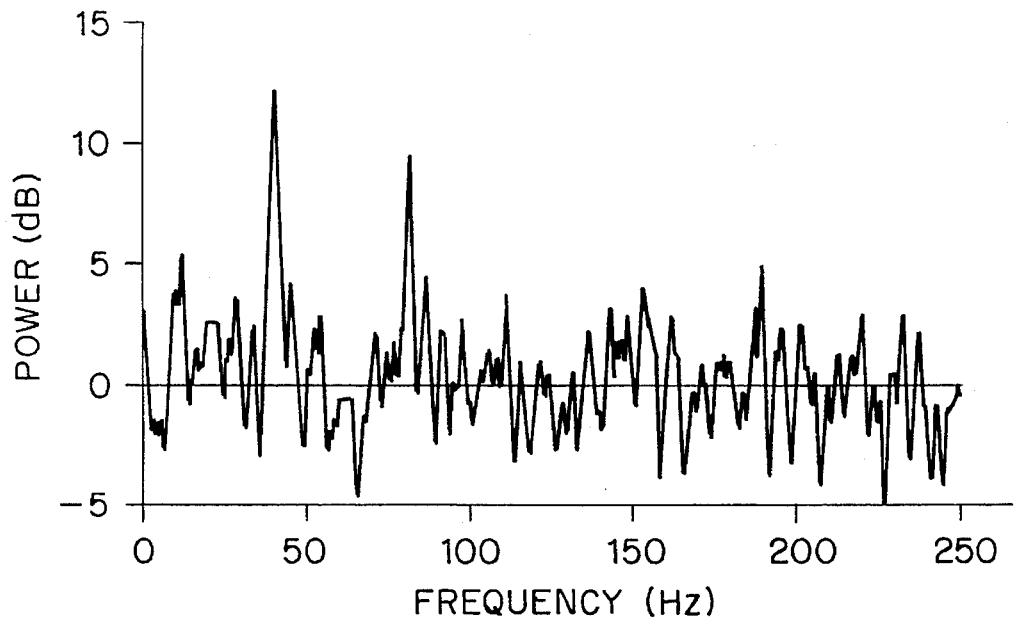
FIG. 13 shows the effect of glucose on the non-linear dielectric spectrum of S. cerevisiae.

As described above, a 3rd harmonic was reproducibly observed with resting cell suspensions of S. cerevisiae. This could be ascribed to the presence of the H+-ATPase in this organism, and should be expected to reflect a situation in which the enzyme was at static head. An experiment to determine how this behaviour might be modified when the enzyme was driven away from static head and was able (or expected) to do work was carried out. Resting cells were taken, their (usual) non-linear dielectric spectrum recorded, and a metabolisable carbon source (D-glucose) added. After a short lag period of some 20 minutes, the spectrum displayed in FIG. 13 was recorded. Remarkably, the 3rd harmonic had disappeared and was replaced by substantial 2nd and 4th harmonics. These even harmonics were also vanadate-sensitive. When static head was again attained, the spectrum, returned to its starting shape, with a substantial 3rd but no even harmonics. This behaviour is consistent with the view that when carrying out net work (energy transduction), the enzyme represents an asymmetric potential well with the rectification necessary for the adsorption of exogenous electric field energy. A parallel measurement of the dielectric permitivity at 0.3 MHz, a monitor of intact cellular biomass, did not show any observable changes during this experiment. Thus non-linear dielectric spectroscopy provides a sensitive means of distinguishing the metabolic states of living cells.

Figure 14:
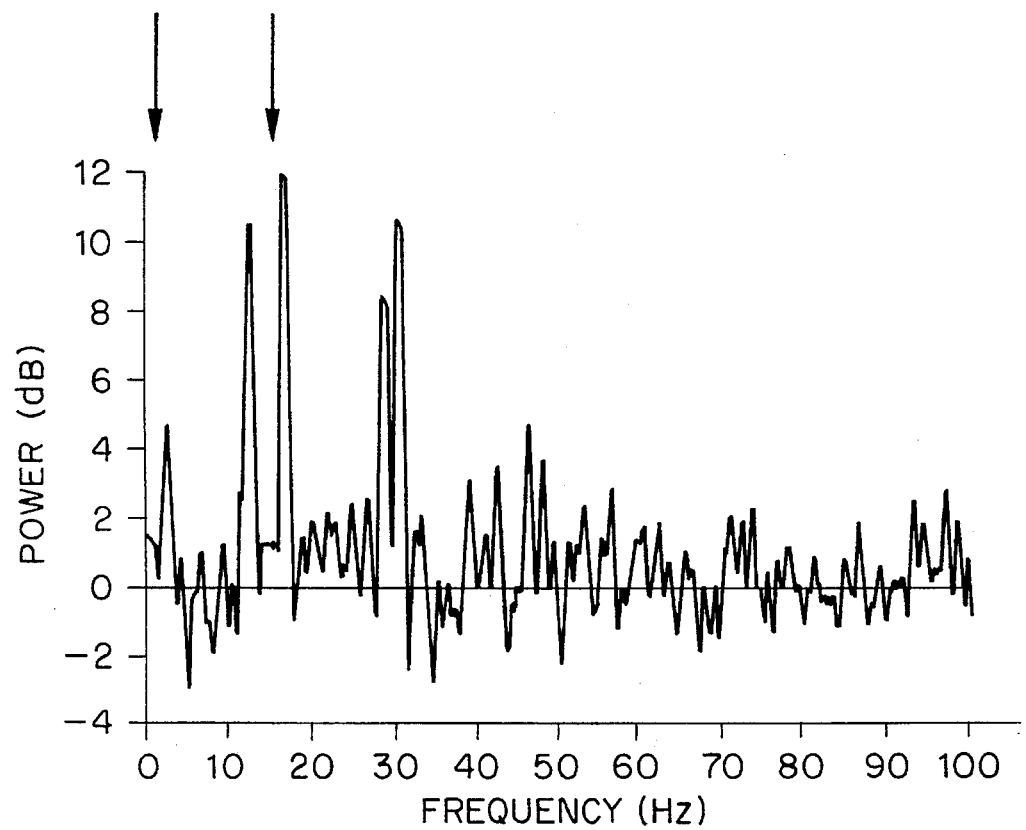
FIG. 14 shows another embodiment of a non-linear dielectric spectrum of S. cerevisiae cells.

Non-linear dielectric properties may also be manifested as the frequency mixing of a plurality of fundamentals. FIG. 14 shows the non-linear dielectric spectrum recorded when a suspension of S. cerevisiae was excited with fields (0.9 V/cm each) at frequencies of 1 Hz and 15 Hz. The frequency mixing to produce signals at sums and differences of integral multiples of the fundamental is clear.

The electric potential $V_m$ generated across the (spherical) yeast plasma membrane is given by $V_m=1.5$ $rE \cos \theta$ where E is the macroscopic field, r the cell radius and $\theta$ the angle between the field and the membrane normal.

For the present cell radius of 3 microns and a field of 2 V.cm$^{-1}$ a maximum (field-dependent change in) membrane potential of 0.9 mV was obtained. For a membrane thickness of 5 nm, the maximum oscillatory transmembrane field $E_m$ is 1800 V.cm$^{-1}$. Typical membrane proteins have permanent dipole moments µ of 100–1000 Debye units. For convenience we will assume that relevant changes in dipole moment due to field-dependent conformational changed of target enzymes are 500 D (they are however likely to be much less since 500 D equates to the displacement of 10 full charges across the membrane). The Langevin factor µE/kT is then equal to some 0.075, i.e. substantially less than 1. Thus despite the application of a field which would normally be regarded as very modest, we have observed the generation of a substantial response frequency by the S. cerevisiae cells.

Figure 15:
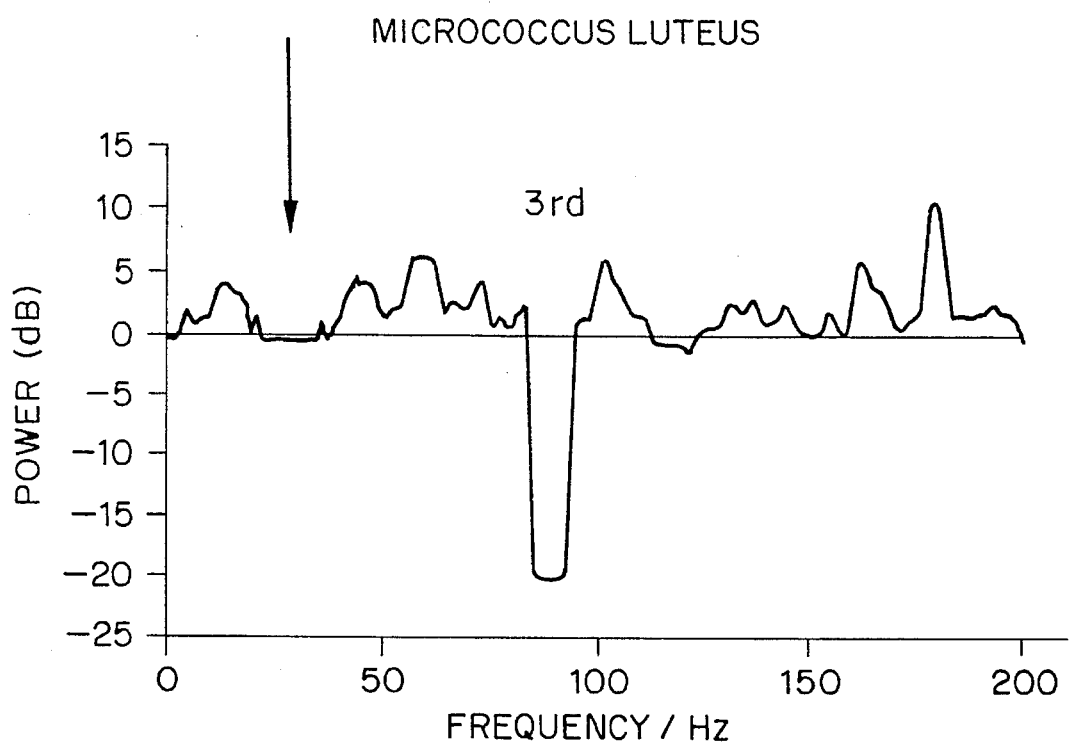
FIG. 15 shows a non-linear dielectric spectrum of an anaerobic suspension of Micrococcus luteus.
Figure 16:
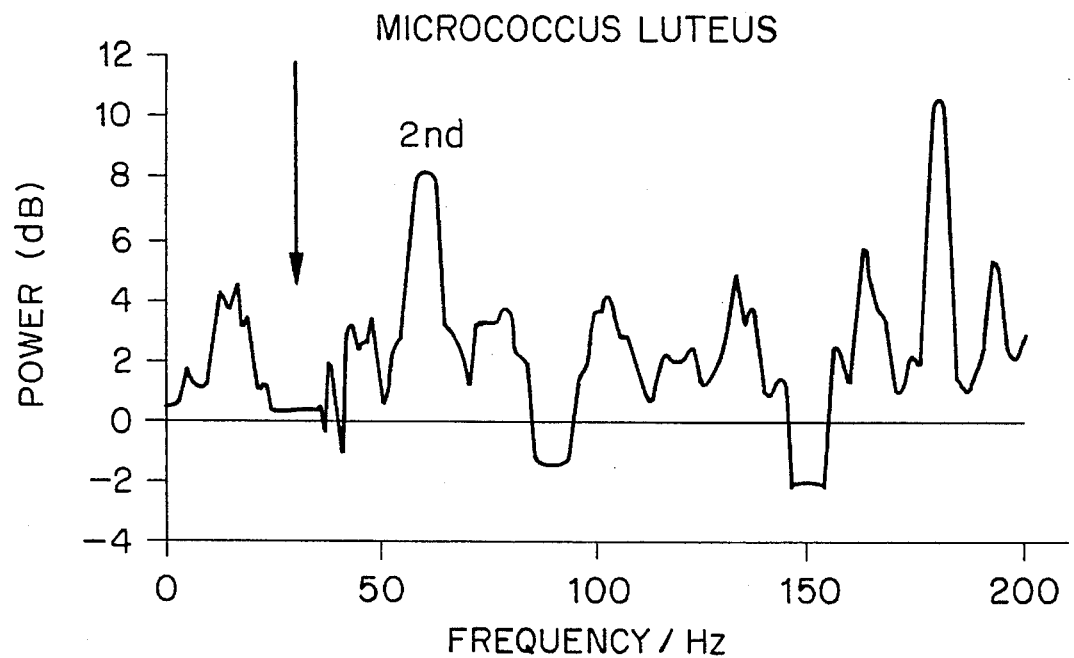
FIG. 16 shows a non-linear dielectric spectrum of an aerobic suspension Micrococcus luteus.

The invention as hereinbefore described has been carried out using suspensions of S. cerevisiae, with or without glucose; however the method is of general applicability and is not limited to the use of the former substrates. FIG. 15 shows a spectrum illustrating the nonlinear dielectric behaviour of an anaerobic suspension of Micrococcus luteus. Since this organism cannot ferment, such cells are resting, and display an odd-numbered (third) harmonic. FIG. 16 shows an aerobic suspension of Micrococcus luteus where the organism can respire and which causes the generation of an even-numbered (second) harmonic.

Substrates which can be determined by the method according to the invention include oxygen, glucose, lactic acid or lactate, or the like. Similarly, inhibitors of cell metabolism can be determined by the method according to the invention; examples of such inhibitors include vanadates, as described above with reference to FIG. 12.

Figure 17:
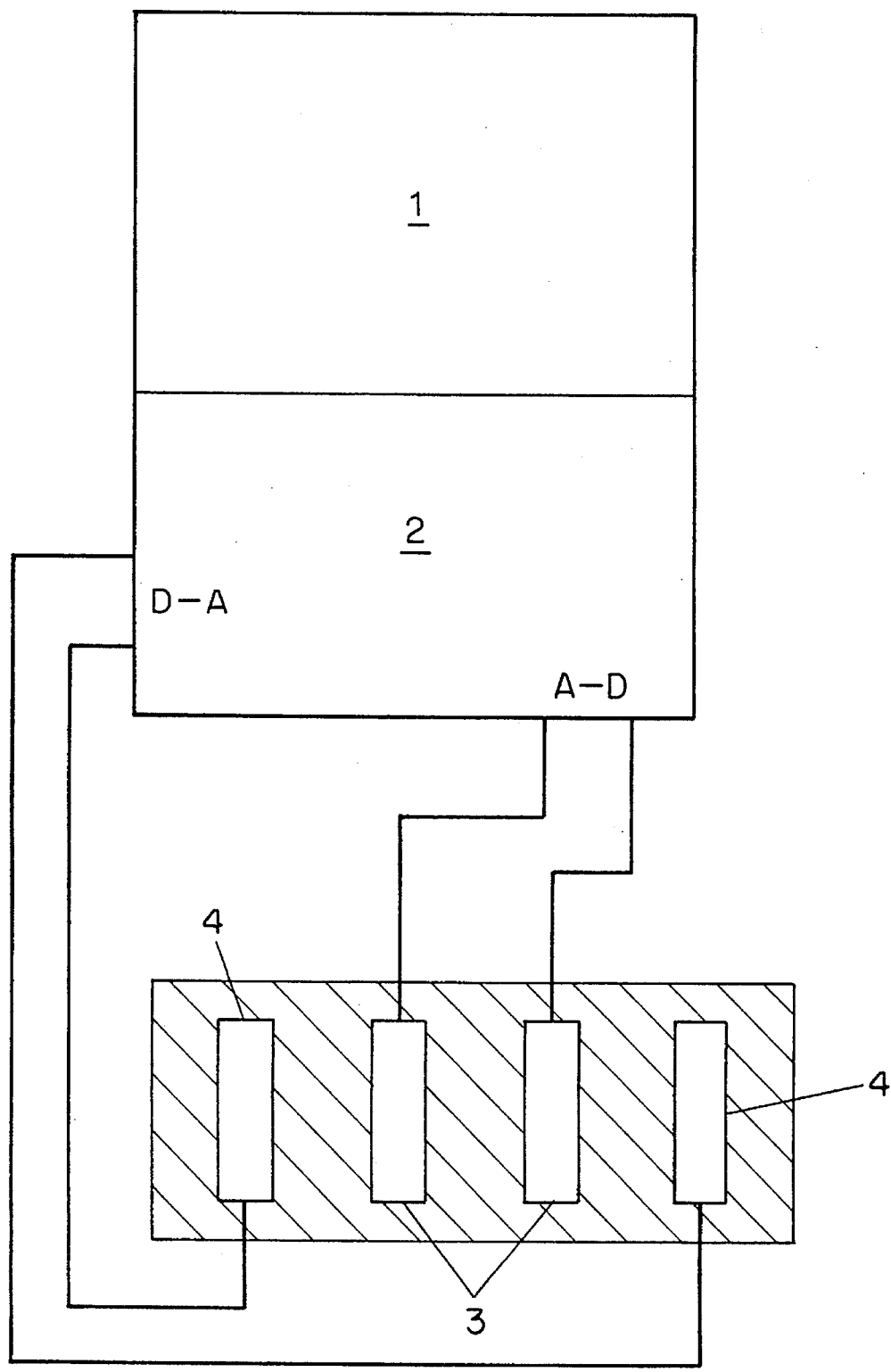
FIG. 17 shows, schematically, certain features of exemplary apparatus according to the invention.

In the embodiment shown in FIG. 17, an AC potential of predetermined frequency may be applied by generator 2 via digital-to-analogue conversion D-A between an outer pair of electrodes 4 in order to excite the system, and cause an alternating potential to arise between the inner pair of electrodes 3. The AC potential arising between the inner pair of electrodes includes harmonics of the excitation frequency. A computer 1 carries out a Fourier transformation on the signal received from the inner pair of electrodes via analogue-to-digital conversion A-D, to determine the power levels at the first five (for example) harmonics. The process may be repeated with different voltages of the excitation signal, and then at different excitation frequencies.

The excitation signal may consist of a sinusoidal waveform. Alternatively the excitation signal may consist of a relatively high DC with a relatively low AC component superimposed on it.

In the following illustrative Example, non-linear dielectric spectroscopy was carried out largely as described above using, in this case, a matrix of 5 voltages, zero-to-peak (as measured on the outer electrodes of apparatus as illustrated in FIG. 17) and 9 frequencies (in Hz), as follows:

| | |
|---|---|
| 0.500000 | |
| 0.750000 | |
| 1.000000 | Voltages |
| 1.250000 | |
| 1.500000 | |
| | |
| 10.000000 | |
| 17.782794 | |
| 31.622777 | |
| 56.234133 | |
| 100.000000 | Frequencies |
| 177.827941 | |
| 316.227766 | |
| 562.341325 | |
| 1000.000000 | |

A sweep consisted of 45 individual spectra, averaging each for 10 blocks. Further sweeps were taken at appropriate intervals. The sampling rate at the inner electrodes was adjusted to be 16 times the value of the frequency applied, such that no windowing was needed and after (Fourier) transformation the power in each consecutive harmonic appears in each consecutive bin. To avoid the need for a reference run (without cells), the following procedure was adopted. The data matrix, consisting of the powers in each of the first 5 harmonics (including the fundamental) at each voltage and frequency, was subjected to multivariate calibration using the partial least squares (PLS) algorithm, fully cross-validated by the leave-one-out method. Such multivariate calibrations are well known to those skilled in the chemometric art.

EXAMPLE

A spot was marked on a human subject's forearm to ensure repeatable placement of a probe with flush electrodes on subsequent sweeps. The probe was also marked to ensure repeatability of orientation. Before each spectrum was taken, the probe was moistened in 150 mM NaCl to ensure good electrical coupling.

Figure 18:
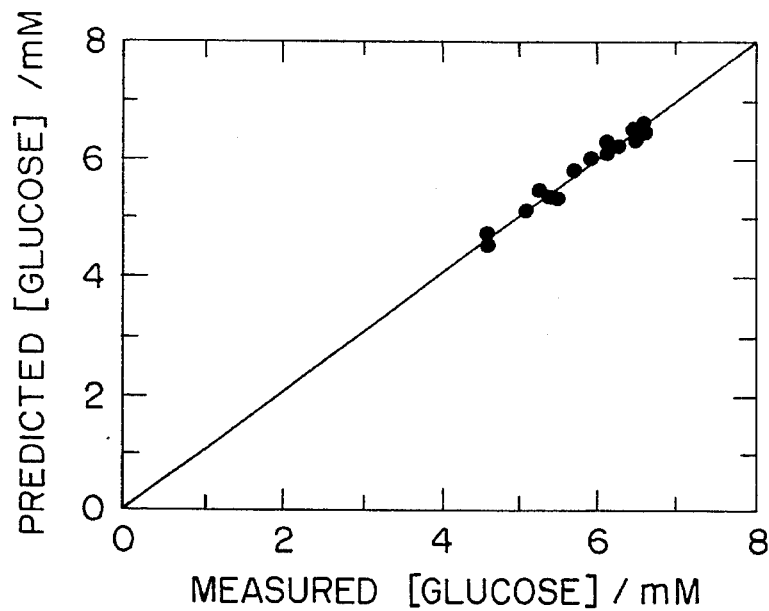
FIGS. 18 to 23 show results achieved in exemplary analyses using method and apparatus according to an embodiment of the invention.

The first two experiments (3 figures) were carried out as follows. Baseline sweeps were taken after the subject had eaten no food for 16 hours, using the same voltages and frequencies as above. Glucose measurements were taken on finger-pricked blood with an optical blood glucose monitoring instrument commercially available under the trade mark "Reflolux" as the reference method. About 100 g of glucose were given orally, and further sweeps taken at approx one minute intervals, checking with the Reflolux instrument every 5 minutes and interpolating these reference readings. To improve the ability of the calibration models to generalise, an iterative method for removing outliers was performed, as follows. First the data from a given run (run 1, me8) were used to make the best model, as judged by cross-validation, leave-one-out self-prediction. The model was used to predict run 2 (me7), and then the points chosen that are closest (within 0.5 mM) to the 1:1 line and the others assumed to be real outliers, i.e. bad data. These "good points" were then used to make a new model, again the best as judged by cross-validated, leave-one-out self-prediction. Finally, a calibration model was formed on the first run with outliers removed according to the revised prediction from the second run. The data for the self model so formed, fully cross validated, using 2 PLS factors, are shown in FIG. 18.

Figure 19:
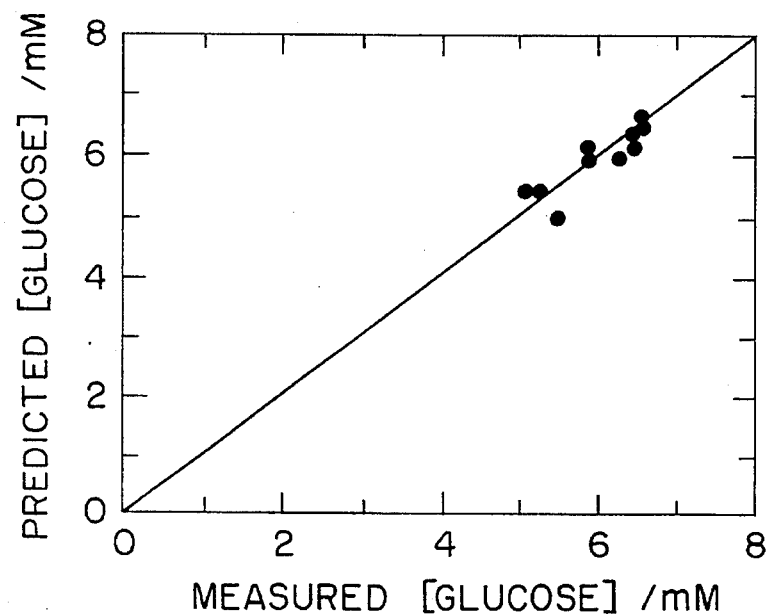
Figure 20:
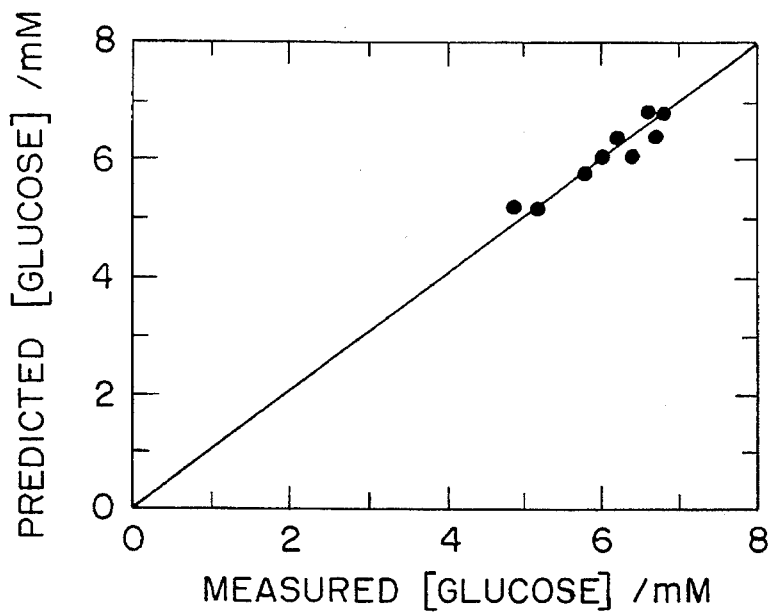

FIG. 19 shows predictions from a calibration model of the same data produced on alternate (odd-numbered) points predicting the even-numbered points from the same run, and FIG. 20 shows the prediction of the pruned dataset of me7 as predicted from the model formed on the pruned dataset of me8.

Figure 21:
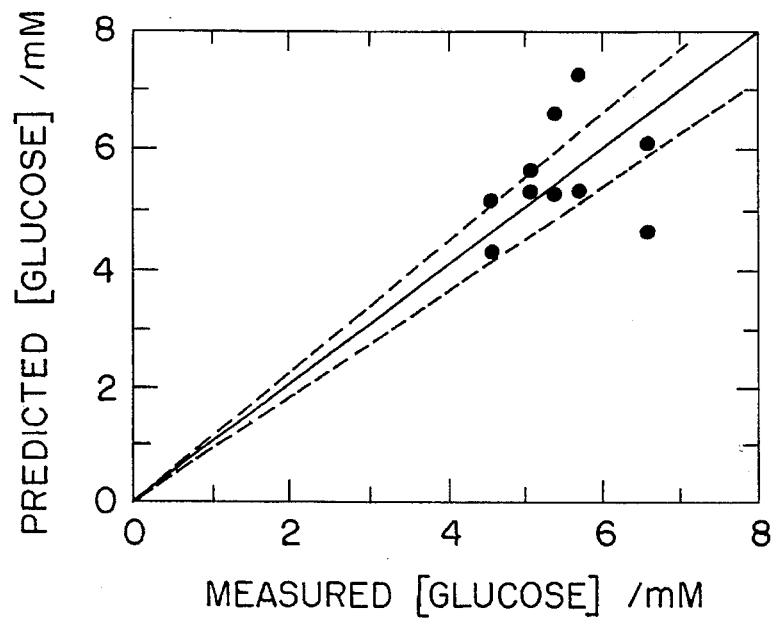

Data were acquired from a separate (diabetic) subject, who had just eaten a meal, his blood glucose followed using the Reflolux instrument and non-linear dielectric spectra acquired as above. The same calibration model (formed on the first subject) was used to predict blood glucose data from the second subject (when these were within the range that had been covered by the calibration model), as shown in FIG. 21 (in which the dotted lines show accuracies of ±10%, the claimed best precision of the reference method).

Figure 22:
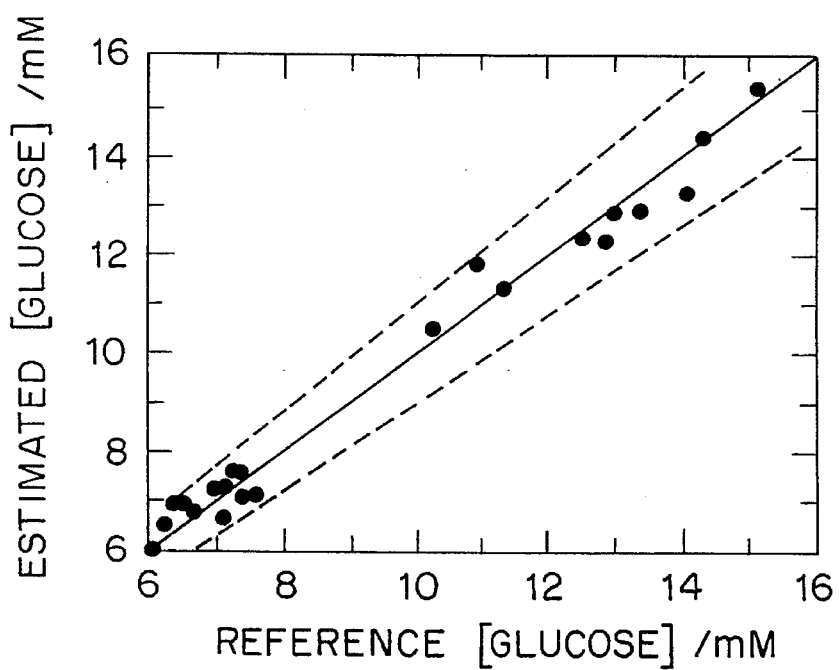
Figure 23:
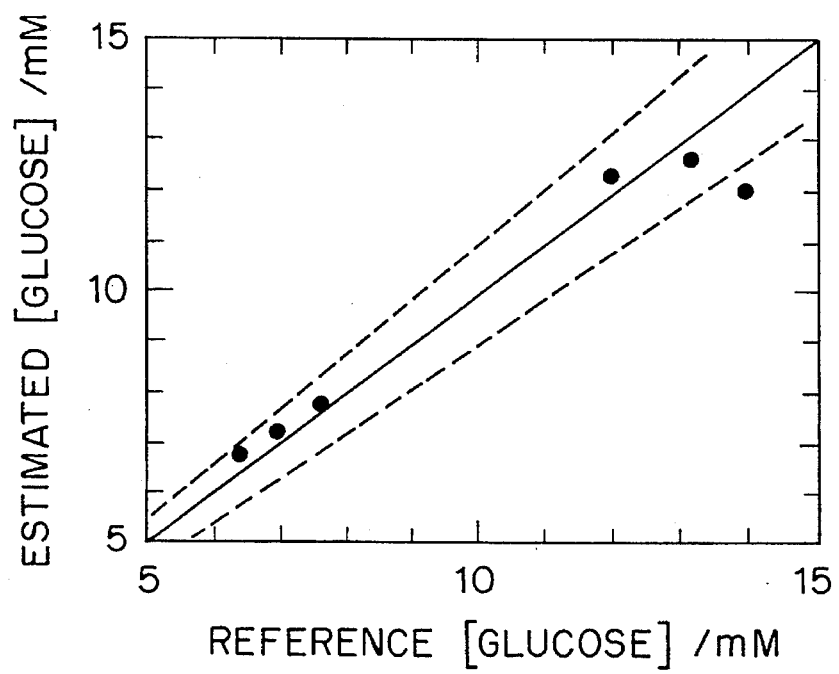

Finally, a combined model was produced for a separate pair of subjects (one diabetic, one non-diabetic). FIG. 22 shows the self-calibration, fully cross-validated, using 5 PLS factors, whilst FIG. 23 shows the predictions using data from the same subjects but which had not been included in the calibration model. In each case, the solid line is the line of identity whilst the dotted lines are identity ±10%, showing that the method according to the invention has excellent predictive power.

We claim:

1. A method of analysing a metabolic state of cellular biological material, said method comprising applying an AC electric potential at one or more discrete frequencies to a sample of the cellular biological material, and determining a response at one or more response frequencies which were substantially absent from the applied AC potential, said one or more response frequencies resulting from a combination of the applied frequency or frequencies.

2. A method according to claim 1, wherein the applied electric potential comprises a first field applied to excite the system, and a second field comprising a probing AC voltage effective to register the field-dependent dielectric properties of the cellular biological material, said first field being of higher magnitude than the second field.

3. A method according to claim 1, wherein said applied AC potential is sinusoidal, and the response frequency or frequencies are observed by performing a translation to ascertain the extent to which the non-linearities of the material are manifest by the generation of harmonics.

4. A method according to claim 1, wherein said material comprises a cell suspension.

5. A method according to claim 1, wherein said material comprises living tissue.

6. A method according to claim 4, wherein said AC electric potential at one or more discrete frequencies is applied to a supernatant of a dispersion or suspension of said cellular biological material suspension, the conductivity of said supernatant being adjusted to be substantially identical to that of said biological material.

7. A method according to claim 1, which method further comprises observing the third harmonic of said response.

8. A method according to claim 1, which method comprises observing even-numbered harmonics of said response.

9. In a method of analysing a metabolic state of cellular biological material, which method comprises applying an electric potential of one or more initial frequencies to the cellular biological material, and measuring a response of the material at at least one response frequency, wherein the improvement comprises that at least one response frequency is substantially not overlapping with the initial frequency or frequencies and results from a combination of the initial frequency or frequencies.

10. A method of analysing or monitoring a determinand associated with cellular biological material, which comprises applying an AC electrical potential at at least one discrete initial frequency to a sample of said material; measuring a response of said material at at least one response frequency substantially not overlapping with said applied potential; and comparing said response with a stored characteristic of said determinand.

11. A method according to claim 10, wherein said determinand is a glucose concentration.

12. Apparatus for analysing a metabolic state of cellular biological material, which apparatus comprises:
    a) retaining means for retaining a sample of said cellular biological material;
    b) means for applying an AC electric potential at one or more discrete frequencies to said sample; and
    c) means for determining a response at one or more response frequencies which were substantially absent from the applied AC potential, said one or more response frequencies resulting from a combination of the applied frequency or frequencies.

13. Apparatus according to claim 12, wherein the means for applying an AC electric potential comprises means for applying a first field effective to excite the biological cell material, and means for applying a probing AC voltage effective to register the field-dependent dielectric properties of the cellular biological material.

14. Apparatus for monitoring or analysing a determinand associated with cellular biological material, which apparatus comprises:
    (a) means for applying an AC electrical potential at one or more discrete frequencies to said material;
    (b) means for determining a response of said material at one or more frequencies which were substantially absent from the applied AC potential; and (c) means for comparing said response to a stored characteristic of said determinand.

15. Apparatus according to claim 14, which further comprises means for retaining said biological material in proximity to said electric potential applying means.

16. Apparatus according to claim 14, wherein said means for retaining the biological material comprises adhesive provided on a patch for retention of an electrode to the skin of a subject.

17. Apparatus according to claim 14, wherein the means for applying an AC electric potential comprises means for applying a field field effective to excite the cellular biological material, and means for applying a probing AC voltage effective to register the field-dependent dielectric properties of the cellular biological material.

18. A method according to claim 1, wherein the metabolic state of the cellular biological material is analyzed in the presence of a substrate for the cellular biological materials.

19. A method according to claim 1, wherein the metabolic state of the cellular biological material is analyzed in the presence of an inhibitor of cell metabolism for said cellular biological material.

20. A method according to claim 1, wherein the electric potential is applied using a plurality of electrodes immersed in a suspension of the biological material.

21. A method according to claim 1, wherein the electric potential is applied using a plurality of electrodes affixed to an exterior surface of a living organism.

22. A method according to claim 9, wherein the electric potential is applied using a plurality of electrodes immersed in a suspension of the biological material.

23. A method according to claim 9, wherein the electric potential is applied using a plurality of electrodes affixed to an exterior surface of a living organism.

* * * * *